(12) United States Patent
Pringle et al.

(10) Patent No.: US 9,947,524 B2
(45) Date of Patent: Apr. 17, 2018

(54) DIATHERMY KNIFE IONISATION SOURCE

(71) Applicant: Micromass UK Limited, Wilmslow (GB)

(72) Inventors: Steven Derek Pringle, Darwen (GB); Michael Raymond Morris, Glossop (GB); Stephen Smith, Stockport (GB); Michael McCullagh, Northwich (GB)

(73) Assignee: MICROMASS UK LIMITED, Wilmslow (GB)

( * ) Notice: Subject to any disclaimer, the term of this patent is extended or adjusted under 35 U.S.C. 154(b) by 0 days.

(21) Appl. No.: 14/727,941

(22) Filed: Jun. 2, 2015

(65) Prior Publication Data
US 2015/0340215 A1    Nov. 26, 2015

Related U.S. Application Data

(63) Continuation of application No. 14/123,548, filed as application No. PCT/GB2012/051259 on Jun. 1, 2012, now Pat. No. 9,053,914.
(Continued)

(30) Foreign Application Priority Data

Jun. 3, 2011  (GB) .................................. 1109414.1

(51) Int. Cl.
*H01J 49/16* (2006.01)
*H01J 49/00* (2006.01)
(Continued)

(52) U.S. Cl.
CPC .............. *H01J 49/16* (2013.01); *A61B 18/14* (2013.01); *H01J 49/0022* (2013.01);
(Continued)

(58) Field of Classification Search
None
See application file for complete search history.

(56) References Cited

U.S. PATENT DOCUMENTS 3,479,545 A * 11/1969 Brewer .................... H01J 27/26
                                                    250/423 R
3,770,954 A * 11/1973 Davis ....................... H01J 49/16
                                                    250/288
(Continued)

FOREIGN PATENT DOCUMENTS

JP      03001435 A  *  1/1991  .............. H01J 49/16
JP      10302710 A  *  11/1998 .............. H01J 49/16
(Continued)

OTHER PUBLICATIONS

Balog et al., "Identification of Biological Tissues by Rapid Evaporative ionization Mass Spectrometry", Anal. Chem. 2010.*
(Continued)

*Primary Examiner* — Michael Logie

(57) ABSTRACT

A method of detecting one or more compounds, chemicals or contaminants in a substrate by mass spectrometry is disclosed. A non-living substrate is analyzed by contacting the substrate with a diathermy knife. An electric current is applied to the diathermy knife such that the diathermy knife vaporizes a portion of the substrate. The vapor is aspirated via a sampling tube pumped by a venturi pump into a vacuum chamber of a mass spectrometer. Analyte molecules are aspirated into the vacuum chamber whereupon they impact a surface of the vacuum chamber and are ionized to form analyte ions which are then mass analyzed.

15 Claims, 7 Drawing Sheets

Related U.S. Application Data

(60) Provisional application No. 61/497,310, filed on Jun. 15, 2011.

(51) Int. Cl.
    H01J 49/10      (2006.01)
    H01J 49/04      (2006.01)
    H01J 49/06      (2006.01)
    A61B 17/32      (2006.01)
    A61B 17/3203    (2006.01)
    A61B 18/00      (2006.01)
    A61B 18/14      (2006.01)
    A61B 18/18      (2006.01)

(52) U.S. Cl.
    CPC .......... *H01J 49/0031* (2013.01); *H01J 49/04* (2013.01); *H01J 49/049* (2013.01); *H01J 49/0459* (2013.01); *H01J 49/06* (2013.01); *H01J 49/10* (2013.01); *A61B 17/3203* (2013.01); *A61B 17/320068* (2013.01); *A61B 2018/00994* (2013.01); *A61B 2018/1412* (2013.01); *A61B 2018/1807* (2013.01); *A61B 2218/008* (2013.01)

(56) References Cited

U.S. PATENT DOCUMENTS

| | | | |
|---|---|---|---|
| H414 H * | 1/1988 | Young | H01J 27/26 250/423 R |
| 4,845,367 A * | 7/1989 | Amirav | H01J 27/26 250/251 |
| 4,935,624 A | 6/1990 | Henion et al. | |
| 5,053,343 A * | 10/1991 | Vora | G01N 27/622 250/287 |
| 5,559,326 A | 9/1996 | Goodley et al. | |
| 6,825,464 B2 | 11/2004 | De La Mora | |
| 6,998,622 B1 * | 2/2006 | Wang | H01J 49/063 250/281 |
| 7,335,897 B2 | 2/2008 | Takats et al. | |
| 7,517,348 B2 | 4/2009 | Vetter et al. | |
| 7,564,028 B2 | 7/2009 | Vestal | |
| 7,718,958 B2 | 5/2010 | Shiea et al. | |
| 7,828,948 B1 | 11/2010 | Hatch et al. | |
| 8,156,151 B2 | 4/2012 | Sidman | |
| 8,193,487 B2 | 6/2012 | Briglin et al. | |
| 8,232,520 B2 | 7/2012 | Cristoni | |
| 8,253,098 B2 | 8/2012 | Hiraoka et al. | |
| 8,286,260 B2 | 10/2012 | Vertes et al. | |
| 8,314,382 B2 | 11/2012 | Takats | |
| 8,334,504 B2 * | 12/2012 | Finlay | H01J 49/0422 250/251 |
| 8,431,409 B1 | 4/2013 | Meinhart et al. | |
| 8,481,922 B2 | 7/2013 | Musselman | |
| 8,778,695 B2 | 7/2014 | Caprioli | |
| 8,803,085 B2 | 8/2014 | Ouyang et al. | |
| 8,834,462 B2 * | 9/2014 | Johnson | A61B 18/042 606/41 |
| 9,046,448 B2 | 6/2015 | Takats | |
| 9,053,914 B2 * | 6/2015 | Pringle | H01J 49/0459 |
| 2002/0008871 A1 | 1/2002 | Poustka | |
| 2002/0070338 A1 | 6/2002 | Loboda | |
| 2002/0076824 A1 | 6/2002 | Haglund, Jr. et al. | |
| 2003/0008404 A1 | 1/2003 | Tomita et al. | |
| 2003/0119193 A1 | 6/2003 | Hess et al. | |
| 2003/0193023 A1 | 10/2003 | Marsh | |
| 2004/0007673 A1 | 1/2004 | Coon et al. | |
| 2004/0124352 A1 | 7/2004 | Kashima et al. | |
| 2004/0235395 A1 | 11/2004 | Hashish et al. | |
| 2005/0017091 A1 | 1/2005 | Olsen et al. | |
| 2005/0032471 A1 | 2/2005 | Pfarr et al. | |
| 2005/0072916 A1 | 4/2005 | Park | |
| 2005/0074361 A1 | 4/2005 | Tanoshima et al. | |
| 2005/0077644 A1 | 4/2005 | Bryan et al. | |
| 2005/0138861 A1 | 6/2005 | O'Connor | |
| 2005/0154490 A1 | 7/2005 | Blaine et al. | |
| 2005/0159765 A1 | 7/2005 | Moutafis et al. | |
| 2005/0178962 A1 | 8/2005 | Guevremont et al. | |
| 2005/0230635 A1 | 10/2005 | Takats et al. | |
| 2005/0258358 A1 | 11/2005 | Thakur | |
| 2006/0035570 A1 | 2/2006 | Chisum et al. | |
| 2006/0091308 A1 | 5/2006 | Boyle et al. | |
| 2006/0097084 A1 | 5/2006 | Gromer et al. | |
| 2006/0108539 A1 * | 5/2006 | Franzen | G01N 27/68 250/423 P |
| 2006/0122593 A1 | 6/2006 | Jun | |
| 2006/0145089 A1 * | 7/2006 | Cristoni | H01J 49/0468 250/423 F |
| 2006/0186334 A1 | 8/2006 | Jolliffe et al. | |
| 2006/0250138 A1 | 11/2006 | Sparkman et al. | |
| 2006/0255264 A1 | 11/2006 | Belford | |
| 2007/0023631 A1 | 2/2007 | Takats | |
| 2007/0023677 A1 | 2/2007 | Perkins et al. | |
| 2007/0114437 A1 | 5/2007 | Kovtoun | |
| 2007/0176113 A1 | 8/2007 | Shiea | |
| 2008/0001081 A1 | 1/2008 | Jindai et al. | |
| 2008/0067352 A1 | 3/2008 | Wang | |
| 2008/0149822 A1 | 6/2008 | Vertes et al. | |
| 2008/0172075 A1 | 7/2008 | Ammann | |
| 2008/0173809 A1 | 7/2008 | Wu | |
| 2008/0234579 A1 | 9/2008 | Halevy-Politch et al. | |
| 2008/0312651 A1 | 12/2008 | Pope et al. | |
| 2009/0065714 A1 | 3/2009 | Keady | |
| 2009/0272893 A1 * | 11/2009 | Hieftje | H01J 49/0463 250/282 |
| 2009/0302211 A1 * | 12/2009 | Takats | G01N 1/286 250/282 |
| 2010/0012830 A1 * | 1/2010 | Cristoni | H01J 49/04 250/282 |
| 2010/0078550 A1 * | 4/2010 | Wiseman | G01N 1/405 250/282 |
| 2010/0186524 A1 * | 7/2010 | Ariessohn | G01N 1/2202 73/863.22 |
| 2011/0036978 A1 * | 2/2011 | Franzen | H01J 49/0422 250/283 |
| 2011/0049352 A1 * | 3/2011 | Ding | H01J 49/0463 250/282 |
| 2012/0080592 A1 * | 4/2012 | Wiseman | G01N 35/1095 250/282 |
| 2012/0156712 A1 * | 6/2012 | Takats | G01N 1/02 435/29 |

FOREIGN PATENT DOCUMENTS

| | | |
|---|---|---|
| JP | 2004/264043 | 9/2004 |
| JP | 2007/170870 | 7/2007 |

OTHER PUBLICATIONS

Berkel, "Thin-Layer Chromatography and El3ectrospray Mass Spectrometry Coupled Using a Surface Sampling probe". Anal. Chem. 2002.*

Keiji et al. "Self-aspirating atmospheric pressure chemical ionization source for direct sampling of analytes on surfaces in liquid solution", Rapid Communications in Mass Spectrometry. 2005.*

Eagles, et al., "Fast Atom Bombardment Mass Spectrometry of Amine Mixtures", John Wiley & Sons, Ltd, 1988.*

Slemr et al., "Concentration Profiles of Diamines in Fresh and aerobically Stored Park and Beef", American Chemical Society, 1985.*

Al Sahaf et al., "*Chemical Composition of Smoke Produced by High-Frequency Electrosurgery*", Irish Journal of Medical Science, vol. 176, No. 3, pp. 229-232, 2007.

Australian Office Action dated Dec. 10, 2013, Australia Patent Application No. 2010252652, 3 pages.

Balog et al., "*Identification of Biological Tissues by Rapid Evaporative Ionization Mass Spectrometry*", Analytical Chemistry, vol. 82, No. 17, pp. 7343-7350, 2010.

Barrett et al., "*Surgical Smoke: A Review of the Literature*", Surgical Endoscopy, vol. 17, No. 6, pp. 979-987, 2003.

(56) References Cited

OTHER PUBLICATIONS

Down, "*A DESI-Rable Ionization Revolutionizes Mass Spectrometry*", Base Peak, 2005.
English Translation of Japanese Office Action, Japanese Patent Application No. 2012-512467, dated Nov. 5, 2013.
Hensman et al., "*Chemical Composition of Smoke Produced by High-Frequency Electrospray in a Closed Gaseous Environment an in Vitro Study*", Surgical Endoscopy, vol. 12, No. 8, pp. 1017-1019, 1998.
Huanwen et al., "*Neutral Desorption Sampling Coupled to Extractive Electrospray Ionization Mass Spectrometry for Rapid Differentiation of Biosamples by Metabolomic Finger Printing*", Journal of Mass Spectrometry, vol. 42, No. 9, pp. 1123-1135, 2007.
Lee et al., "*Thermally Assisted Electrospray Interface for Liquid Chromatography/Mass Spectrometry*", Rapid Communications in Mass Spectrometry, vol. 6, pp. 727-733, 1992.
McEwen et al., "*Analysis of Solids, Liquids, and Biological Tissues Using Solids Probe Introduction at Atmospheric Pressure on Commercial LC/MS Instruments*", Anal. Chem., vol. 77, pp. 7826-7831, 2005.
Moot et al., "*Composition of Volatile Organic Compounds in Diathermy Plume as Detected by Selected Ion Flow Tube Mass Spectrometry*", ANZ Journal of Surgery, vol. 77, No. 1-2, pp. 20-23, 2007.
PCT International Search Report and Written Opinion for International Appln. No. PCT/IB2012/003009, dated Aug. 14, 2013, 6 pages.
PCT International Search Report and Written Opinion for International Appln. No. PCT/IB2010/001261, dated Sep. 21, 2010, 5 pages.
PCT International Search Report and Written Opinion for International Appln. No. PCT/IB2012/002995, dated Sep. 10, 2013, 3 pages.
Qiao et al., "*Electrostatic-Spray Ionization Mass Spectrometry*", Analytical Chemistry, vol. 84, No. 17, pp. 7422-7430, 2012.
Sabine et al., "*Electrospray Post-Ionization Mass Spectrometry of Electrosurgical Aerosols*", Journal of American Society of Mass Spectrometry, vol. 22, No. 11, pp. 2082-2089, 2011.
Sakairi et al., "*Characteristics of a Liquid Chromatograph/Atmospheric Pressure Ionization Mass Spectrometer*", Anal. Chem., vol. 60, pp. 774-780, 1988.
Takats et al., "*Characterization of DESI-FTICR Mass Spectrometry—From ECD to Accurate Mass Tissue Analysis*", Journal of Mass Spectrometry, vol. 43, pp. 196-203, 2008.
Takats et al., "*Mass Spectrometry Sampling Under Ambient Conditions with Desorption Electrospray Ionization*", Science, vol. 306, 2004.
Tottszer et al., "*Laser Heating Versus Resistive Heating in the Field-Desorption Mass Spectrometry of Organic Polymers*", J. Phys. D: Appl. Phys., vol. 21, pp. 1713-1720, 1988.
Written Opinion of the International Searching Authority, for International Application No. PCT/IB2012/002995, dated Sep. 10, 2013, 6 pages.
Mulligan, Christopher C. et al., "Desorption electrospray ionization with a portable mass spectrometer: in situ analysis of ambient surfaces", Chemical Communications—Chemcom, No. 16, pp. 1709-1711, (Jan. 2006).

\* cited by examiner

DIATHERMY KNIFE IONISATION SOURCE

CROSS-REFERENCE TO RELATION APPLICATIONS

This application is a continuation application of U.S. patent application Ser. No. 14/123,548, filed 3 Dec. 2013, which is the National Stage of International Application No. PCT/GB2012/051259, filed 1 Jun. 2012, which claims priority from and the benefit of U.S. Provisional Patent Application Ser. No. 61/497,310 filed on 15 Jun. 2011 and United Kingdom Patent Application No. 1109414.1 filed on 3 Jun. 2011. The entire contents of these applications are incorporated herein by reference.

BACKGROUND OF THE PRESENT INVENTION

The present invention relates to a method of mass spectrometry and a mass spectrometer. The preferred embodiment relates to the use of a diathermy knife for vaporising a sample which is subsequently ionised within a vacuum chamber of a mass spectrometer and is then mass analysed.

Electrosurgical knives are known for use in surgical procedures on living patients. An electrosurgical knife is a device in which a high frequency electric current is applied to an electrode, typically a metallic blade or pincers. The electrode of the knife is then used in surgery for tissue ablation, cutting or coagulation.

Diathermy is concerned with using an electric current to generate a source of heat for therapeutic applications.

It is desired to provide an improved method of mass spectrometry.

SUMMARY OF THE INVENTION

According to an aspect of the present invention there is provided a method of mass spectrometry comprising:

contacting a substrate with an electrode and applying an electric current to the electrode to generate gas phase analyte molecules;

causing the gas phase analyte molecules to be ionised to form analyte ions; and mass analysing the analyte ions.

The method preferably further comprises contacting the substrate with the electrode at atmospheric pressure.

The method preferably further comprises providing a hand-held device comprising the electrode.

The method preferably further comprises manually contacting the substrate with the electrode.

The step of applying the electric current to the electrode preferably causes a portion of the substrate to vaporise and form the gas phase analyte molecules.

The electrode preferably comprises a diathermy knife or an electrosurgical RF knife.

The electrode preferably has a pointed protrusion or a cutting edge for cutting or penetrating the substrate.

At least a portion of the substrate that is contacted with the electrode preferably contains a proportion of water or another liquid.

The method preferably further comprises applying a fluid to at least a portion of the substrate prior to contacting the substrate with the electrode.

According to an embodiment after applying the fluid, the substrate is allowed to at least partially dry before contacting the substrate with the electrode.

The fluid may comprise a saline solution.

The fluid may comprise a solvent and/or water.

At least the portion of the substrate that is contacted with the electrode is preferably electrically conductive.

The method preferably further comprises:

contacting different regions of the substrate with the electrode so as to generate gas phase analyte molecules from the different regions;

causing the gas phase analyte molecules from the different regions to be ionised to form analyte ions; and mass analysing the analyte ions from the different regions.

The different regions of the substrate preferably comprise different regions on the surface of the substrate and/or different regions below the surface of the substrate.

According to an aspect of the present invention there is provided a method of mass spectrometry comprising:

probing a substrate with an ultrasonic probe to generate gas phase analyte molecules;

causing the gas phase analyte molecules to be ionised to form analyte ions; and mass analysing the analyte ions.

The method preferably further comprises probing the substrate with the ultrasonic probe at atmospheric pressure.

The method preferably further comprises providing a hand-held device comprising the ultrasonic probe.

The method preferably further comprises manually probing the substrate with the ultrasonic probe.

According to an aspect of the present invention there is provided a method of mass spectrometry comprising:

probing a substrate with a laser probe to generate gas phase analyte molecules;

transmitting the gas phase analyte molecules into a vacuum chamber of a mass spectrometer;

causing the gas phase analyte molecules to be ionised within the vacuum chamber to form analyte ions; and mass analysing the analyte ions.

The method preferably further comprises probing the substrate with the laser probe at atmospheric pressure.

The method preferably further comprises providing a hand-held device comprising the laser probe.

The method preferably further comprises manually probing the substrate with the laser probe.

According to an aspect of the present invention there is provided a method of mass spectrometry comprising:

contacting a substrate with a jet of fluid to generate gas phase analyte molecules;

transmitting the gas phase analyte molecules into a vacuum chamber of a mass spectrometer;

causing the gas phase analyte molecules to be ionised within said vacuum chamber to form analyte ions; and mass analysing the analyte ions.

The method preferably further comprises contacting the substrate with the jet of fluid at atmospheric pressure.

The method preferably further comprises providing a hand-held device which is arranged to emit the jet of fluid.

The method preferably further comprises manually directing the hand-held device so as to direct the jet of fluid onto the substrate.

The fluid preferably comprises a liquid.

The liquid preferably comprises water or an aqueous solution.

According to another embodiment the fluid comprises one or more gases.

The method preferably further comprises aspirating the gas phase analyte molecules into a mass spectrometer.

The method preferably further comprises aspirating the gas phase analyte molecules via a tube or supply line into the mass spectrometer.

The method preferably further comprises using a pump to draw the gas phase analyte molecules into the mass spectrometer. According to the preferred embodiment the pump is not directly connected to an exhaust port of a vacuum chamber.

The method preferably further comprises using a venturi pump to draw the gas phase analyte molecules into the mass spectrometer.

The method preferably further comprises causing the gas phase analyte molecules to pass into a vacuum chamber of the mass spectrometer.

The method preferably further comprises causing the gas phase analyte molecules to be ionised within the vacuum chamber of the mass spectrometer to form the analyte ions.

The gas phase analyte molecules are preferably ionised upon impacting a surface of or within the vacuum chamber.

The gas phase analyte molecules are preferably ionised upon impacting an RF ion-optical component located within the vacuum chamber.

The RF ion-optical component preferably comprises an ion guide or ion trap.

The gas phase analyte molecules may be ionised by an ion source located within the vacuum chamber.

The method preferably further comprises using a portable mass spectrometer to perform the step of mass analysing the analyte ions.

The substrate preferably comprises a non-living substrate.

The substrate preferably comprises a non-human and/or non-animal substrate.

The method comprises a non-surgical method.

The method comprises a non-therapeutic method.

The method preferably further comprises seeking to detect one or more compounds, chemicals or contaminants in the substrate.

The method preferably further comprises identifying one or more compounds, chemicals or contaminants in the substrate by mass analysing the analyte ions.

The method may be used to detect the presence of one or more predetermined compounds, chemicals or contaminants in the substrate.

The method preferably further comprises detecting if one or more compounds, chemicals or contaminants are present in the substrate above a predetermined concentration.

At least one of the compounds, chemicals or contaminants may comprise a pesticide, a steroid or other drug, chloramphenicol, a bulking material, a mycotoxin or water born pathogen, histamine, putrescine or cadaverine.

The substrate may comprise a food product.

The method preferably further comprises determining the freshness of the food product by detecting the presence and/or concentration of one or more compounds, chemicals or contaminants in the substrate.

The method preferably further comprises detecting the presence and/or concentration of histamine, putrescine or cadaverine.

The substrate may comprise a pharmaceutical tablet or other pharmaceutical product.

The method preferably further comprises detecting one or more active ingredients and/or bulking agents in the substrate.

The substrate preferably comprises a solid, gel or powder.

The substrate may comprise a dead biological organism.

According to an aspect of the present invention there is provided a mass spectrometer comprising:

an electrode which, in use, is brought or moved into contact with a substrate;

a device arranged and adapted to apply an electric current to the electrode so as to generate gas phase analyte molecules from the substrate;

a device arranged and adapted to cause the gas phase analyte molecules to be ionised to form analyte ions; and a mass analyser for mass analysing the analyte ions.

The electrode preferably comprises a diathermy knife or an electrosurgical RF knife.

According to an aspect of the present invention there is provided a mass spectrometer comprising:

an ultrasonic probe arranged and adapted to probe a substrate so as to generate gas phase analyte molecules from the substrate;

a device arranged and adapted to cause the gas phase analyte molecules to be ionised to form analyte ions in use; and a mass analyser for mass analysing the analyte ions.

The device arranged and adapted to cause the gas phase analyte molecules to be ionised to form analyte ions in use preferably comprises an internal surface of a vacuum chamber and/or an RF ion-optical component within a mass spectrometer. According to another embodiment the device may comprise an ion source located within a vacuum chamber of a mass spectrometer.

According to an aspect of the present invention there is provided a mass spectrometer comprising:

a laser probe arranged and adapted to probe a substrate so as to generate gas phase analyte molecules from the substrate;

a device arranged and adapted to transmit the gas phase analyte molecules into a vacuum chamber of a mass spectrometer;

a device arranged and adapted to cause the gas phase analyte molecules to be ionised within the vacuum chamber to form analyte ions; and a mass analyser for mass analysing the analyte ions.

According to an aspect of the present invention there is provided a mass spectrometer comprising:

a device for directing a jet of fluid so as to contact a substrate and to generate gas phase analyte molecules from the substrate in use;

a device arranged and adapted to transmit the gas phase analyte molecules into a vacuum chamber of a mass spectrometer;

a device arranged and adapted to cause the gas phase analyte molecules to be ionised within the vacuum chamber to form analyte ions; and a mass analyser for mass analysing the analyte ions.

The device arranged and adapted to cause the gas phase analyte molecules to be ionised to form analyte ions in use preferably comprises an internal surface of a vacuum chamber and/or an RF ion-optical component within a mass spectrometer. According to another embodiment the device may comprise an ion source located within a vacuum chamber of a mass spectrometer.

According to an aspect of the present invention there is provided a method comprising:

contacting and/or cutting a non-living substrate at atmospheric pressure with a hand-held electrosurgical knife comprising an electrode, wherein the substrate comprises a solid, gel or powder;

applying an electric current to the electrode in order to vaporise a portion of the substrate and to generate gas phase analyte molecules from the substrate;

transferring the gas phase analyte molecules into a vacuum chamber of a mass spectrometer;

ionising the gas phase analyte molecules within the vacuum chamber to form analyte ions; and mass analysing the analyte ions.

According to an aspect of the present invention there is provided apparatus comprising:

a hand-held electrosurgical knife comprising an electrode, wherein in use the electrode is arranged and adapted to contact and/or cut a non-living substrate at atmospheric pressure, wherein the substrate comprises a solid, gel or powder;

a device arranged and adapted to apply an electric current to the electrode in order to vaporise, in use, a portion of the substrate and to generate gas phase analyte molecules from the substrate;

a device arranged and adapted to transfer the gas phase analyte molecules into a vacuum chamber of a mass spectrometer;

a device arranged and adapted to ionise the gas phase analyte molecules within the vacuum chamber to form analyte ions; and a mass analyser for mass analysing the analyte ions.

According to an aspect of the present invention there is provided a method of detecting one or more compounds, chemicals or contaminants in a substrate by mass spectrometry, the method comprising:

providing a non-living substrate to be analysed;

contacting the substrate with an electrode;

applying an electric current to the electrode such that the electrode ionises a portion of the substrate so as to generate ions therefrom; and mass analysing the ions.

The method preferably further comprises vaporising and/or ionising the portion of the substrate with the electrode when the current is applied.

The method preferably further comprises identifying the one or more compounds, chemicals or contaminants in the substrate based on the mass analysing step.

According to another aspect of the present invention there is provided a mass spectrometer comprising:

an ionisation source comprising a diathermy knife; and a mass analyser.

It will be understood by those skilled in the art that the gas phase analyte molecules which are preferably transferred in a vacuum chamber of the mass spectrometer are preferably neutral or uncharged and should be distinguished from ions which have a net charge.

The present invention recognizes that diathermy knives may be used as general purpose ionization sources and have applicability in the field of mass spectrometry outside of the surgical environment, in particular in the area field portable mass spectrometry.

It is believed that some charged droplets (both positive and negative) may be formed as the substrate is vaporized by the diathermy knife or other device. However, whilst ions may well be generated directly by the knife with the preferred arrangement it is unlikely that the ions which are subsequently mass analysed are those same ions which were formed at the point of contact between the knife and the substrate. In particular, it is unlikely that ions formed by the knife would be able to be transported at atmospheric pressure along the length of a sampling tube into a mass spectrometer. Less preferred embodiments are, however, contemplated wherein the electrosurgical knife may probe and/or cut a substrate immediately in front of an ion inlet into a mass spectrometer and at least some ions may be transmitted through the ion inlet and be subsequently mass analysed.

It is believed that fumes or analyte molecules from the substrate which are aspirated into the initial vacuum chamber of a mass spectrometer are ionised upon impacting either the (internal) wall of the initial vacuum chamber housing and/or an ion-optical component such as an ion guide located within a vacuum chamber downstream of the initial vacuum chamber. Although analyte ions may be created by other means including directly at the site that the RF electrosurgical knife contacts a substrate it is believed that at least the most dominant process of ionisation is by the analyte molecules impacting a surface and becoming ionised as a result of the impact with the surface.

It is apparent, therefore, that the present invention represents a significant advance in the art and enables a hand-held and portable device to be used in the testing of e.g. food and pharmaceutical products at e.g. ports of entry into a country or during the course of a safety inspection.

The suitability of a substrate to be analyzed by the preferred technique depends somewhat upon its conductivity. Ideally, the sampled area should be moist but not wet. However, embodiments are contemplated wherein dry substrates may be analysed after being moistened with a saline solution. As the ionization is restricted spatially to the area of a knife electrode tip, mass spectra from various parts of the sample may be easily collected. For example, the skin of an apple may initially be examined for pesticides, and then cut into with the electrode in order to analyse the core region. As such, the preferred device may form part of a small field portable mass spectrometer for use at point of entry, site inspections and process control.

Government agencies mandate maximum permitted levels of contaminants in food products. According to an embodiment, the preferred device and method may be used to detect contaminants in food products. Examples include, but are not limited to, detecting pesticides in fruit and vegetables, steroids and veterinary drugs in meat and chloramphenicol in foods such as prawns and chicken.

In another preferred embodiment, the preferred device and method may be used to detect unwanted (and potentially dangerous and/or illegal) bulking materials in food, such as pork gelatin in chicken.

In other embodiments, the preferred device and method may be used to detect mycotoxins and water born pathogens in seafood or histamine in cheese and fish.

In a preferred embodiment the preferred device and method may be used to monitor and/or test the freshness of meat or fish, for example, by detecting the presence and/or concentration of histamine, putrescine or cadaverine, etc.

In another embodiment the preferred device and method may be used to detect active ingredients or other compounds in pharmaceutical products. For example, a preferred method may comprise moistening a pharmaceutical tablet using standard HPLC solvents (e.g. with 50% mixture of methanol and water) and then obtaining mass spectra. This technique may be used to quickly detect active ingredients and bulking agents.

According to an embodiment the mass spectrometer may further comprise:

(a) an ion source and/or an additional ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS")

ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; and (xx) a Glow Discharge ("GD") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser; (x) a Fourier Transform electrostatic or orbitrap mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass fitters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wein filter; and/or (k) a device or ion gate for pulsing ions; and/or (l) a device for converting a substantially continuous ion beam into a pulsed ion beam.

The mass spectrometer may further comprise either:

(i) a C-trap and an Orbitrap® mass analyser comprising an outer barrel-like electrode and a coaxial inner spindle-like electrode, wherein in a first mode of operation ions are transmitted to the C-trap and are then injected into the Orbitrap® mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the Orbitrap® mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

BRIEF DESCRIPTION OF THE DRAWINGS

Various embodiments of the present invention will now be described, by way of example only, and with reference to the accompanying drawings in which.

DETAILED DESCRIPTION OF PREFERRED EMBODIMENTS

A preferred embodiment of the present invention will now be described with reference to FIG. 1.

Figure 1:
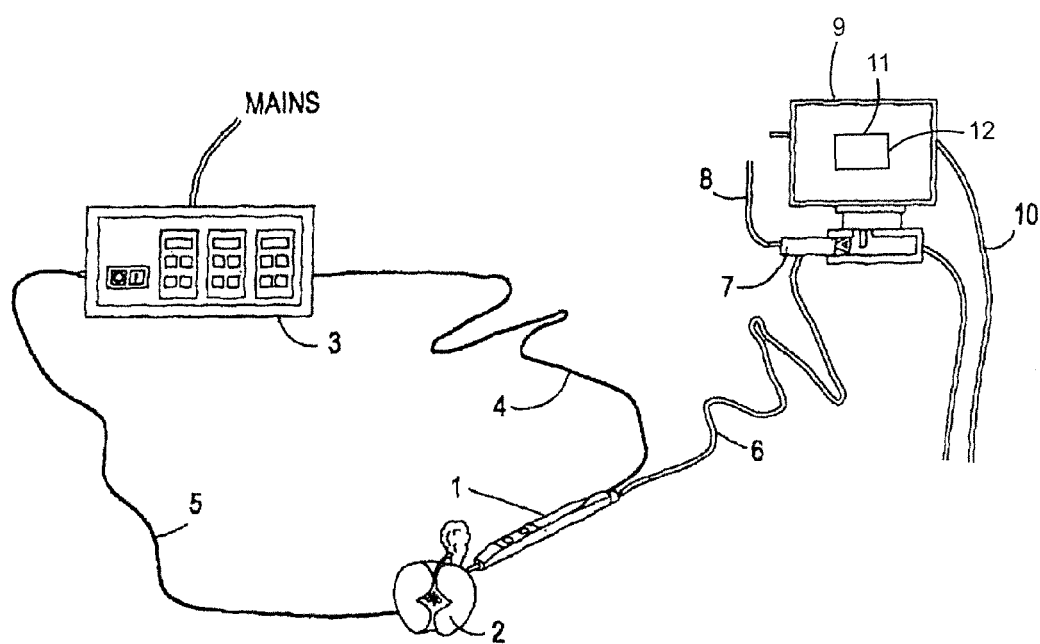
FIG. 1 shows a preferred embodiment of the present invention wherein an electrosurgical RE knife is used to cut an apple and fumes from the cutting process are extracted via a sampling tube which is aspirated by a venturi pump so that the fumes are passed into a mass spectrometer.

FIG. 1 shows a preferred embodiment of the present invention wherein an electrosurgical RF knife 1 is used to cut a substrate which for sake of example only may comprise an apple 2. The electrosurgical RF knife 1 is powered by an electrosurgery unit 3. The electrosurgical RF knife 1 is connected to the electrosurgery unit via a knife feed (floating) 4 and a knife return (floating) 5. The electrosurgical RF knife 1 has a sampling tube 6 which enables fumes comprising analyte molecules resulting from the cutting process to be extracted. The sampling tube 6 is preferably aspirated by a venturi pump 7 which is supplied with an air supply 8. The fumes and analyte molecules from the substrate resulting from the probing and/or cutting process pass along the sampling tube 6 and pass into a mass spectrometer 9 having a rotary pump exhaust 10. At least a portion of the gas phase analyte molecules are ionised within a vacuum chamber 11 of the mass spectrometer 9 to form the analyte ions. The gas phase analyte molecules are preferably ionised upon impacting a surface 12 of or within the vacuum chamber 11.

In order to illustrate the utility of the preferred embodiment to analysing food products, apple segments were dosed with a mix of 21 pesticides at various concentrations (100, 10 and 1 ng/μl). The apple segments were then analysed using a diathermy knife or RF electrode knife in combination with a modified Waters® G2 QToF mass spectrometer in a manner similar to that shown in FIG. 1 except that the sampling tube 6 was not utilised.

A total of 100 μl of the mixture of pesticides was spread over the apple surface and was allowed to soak in and dry. A 1 cm$^2$ area of the apple was then analysed by applying the diathermy knife or RF electrode knife to it (setting coag. 30). The apple segment was held in front of the sample cone of the mass spectrometer and in this particular experiment no attempt was made to trap or funnel the smoke plume from the apple into the mass spectrometer.

The table below shows the 21 pesticides which were used at concentrations of 100 ng/μl together with an indication as to whether or not they were detected.

| Compound name | Formula | M + H | Detected |
| --- | --- | --- | --- |
| Pirimiphos-methyl | C11H20N3O3PS | 306.1041 (1+) | yes |
| Profenofos | C11H15BrClO3PS | 372.9430 (1+) | no |
| Prometon | C10H19N5O | 226.1668 (1+) | yes |
| Prometryn | C10H19N5S | 242.1439 (1+) | yes |
| Propamocarb | C9H20N2O2 | 189.1603 (1+) | yes |
| Propaquizafop | C22H22ClN3O5 | 444.1326 (1+) | no |
| Pyraclostrobin | C19H18ClN3O4 | 388.1064 (1+) | no |
| Pyrazophos | C14H20N3O5PS | 374.0940 (1+) | yes |
| Quinmerac | C11H8ClNO2 | 222.0322 (1+) | yes |
| Quizalofop-ethyl | C19H17ClN2O4 | 373.0955 (1+) | no |
| Siduron | C14H20N2O | 233.1654 (1+) | yes |
| Spiroxamine | C18H35NO2 | 298.2746 (1+) | yes |
| Sulfotep | C8H20O5P2S2 | 323.0306 (1+) | no |
| Tebufenozide |  | 353.2229 | yes |
| Tebuthiuron | C9H16N4OS | 229.1123 (1+) | yes |
| Terbufos | C9H21O2PS3 | 289.0520 (1+) | no |
| Terbumeton | C10H19N5O | 226.1668 (1+) | yes |
| Tetrachlorvinphos | C10H9Cl4O4P | 364.9071 (1+) | no |
| Thiabendazole | C10H7N3S | 202.0439 (1+) | yes |
| Triticonazole | C17H20ClN3O | 318.1373 (1+) | yes |
| Zoxamide | C14H16Cl3NO2 | 336.0325 (1+) | no |

Figure 2A:
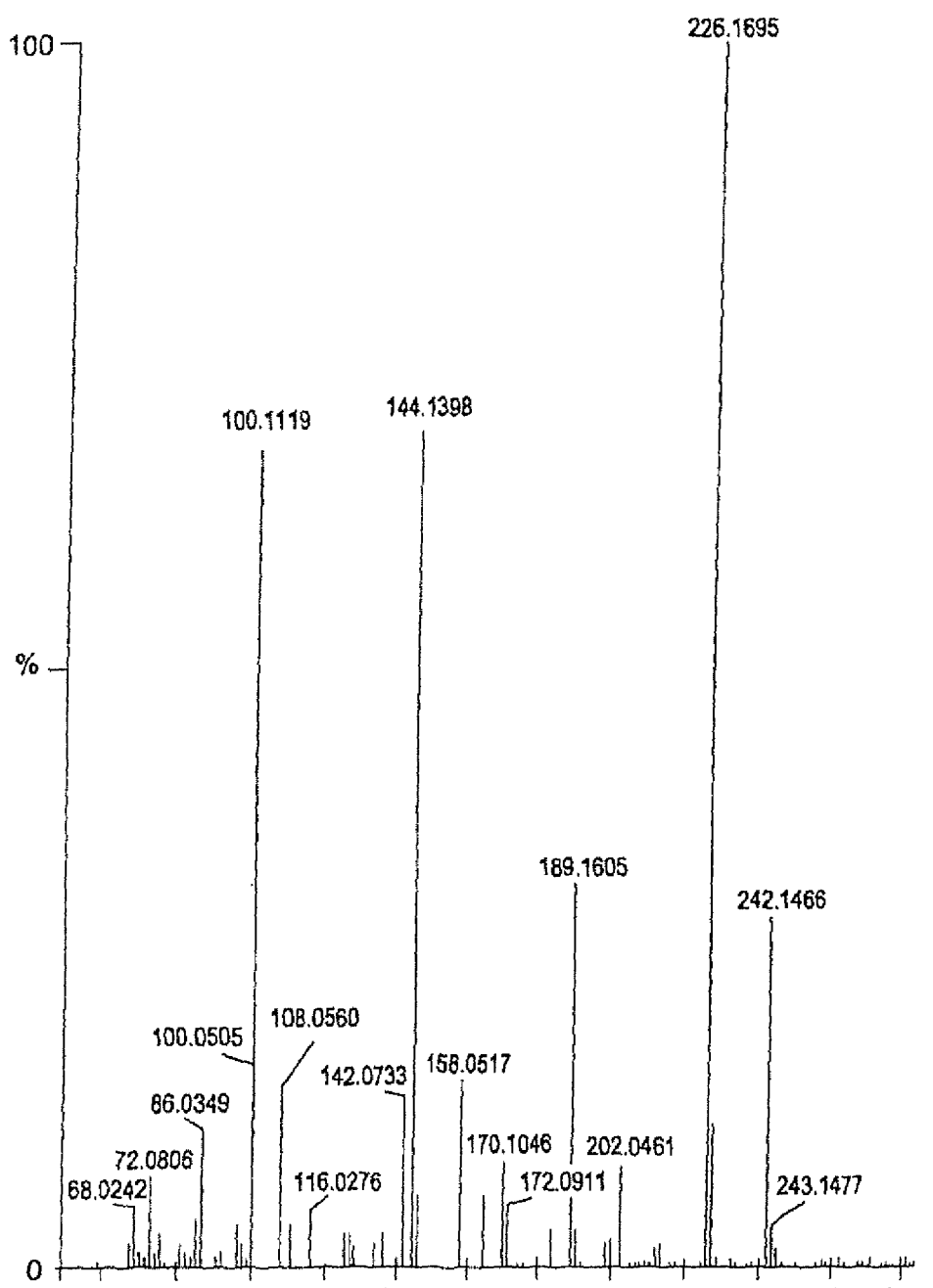
FIGS. 2A, 2B and 2C show a mass spectrum obtained according to a preferred embodiment of the present invention wherein an apple is analysed to detect various pesticides.
Figure 2B:
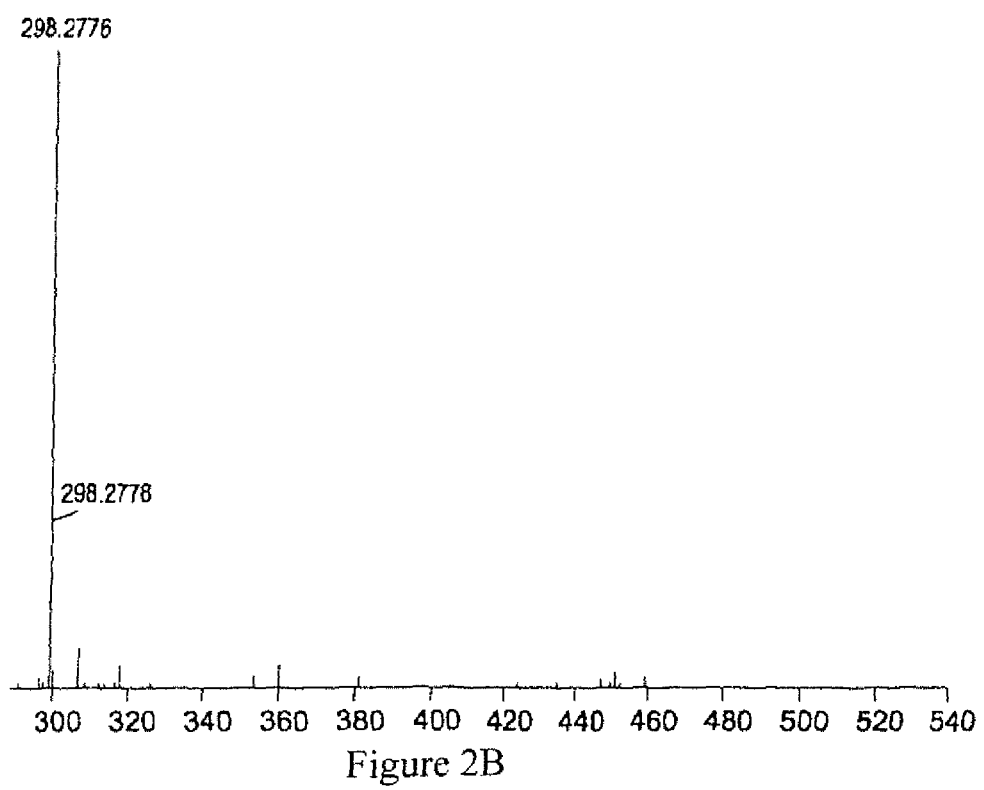
Figure 2C:
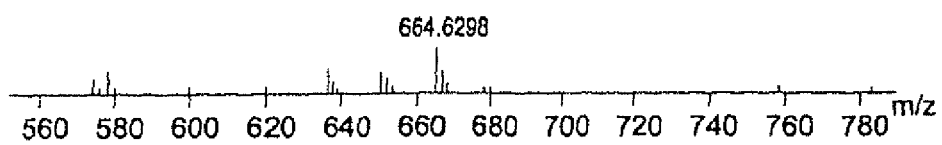

FIG. 2 shows FIGS. 2A, 2B and 2C show a mass spectrum which was obtained when analysing the apple contaminated with a mixture of 21 pesticides using an electric knife according to an embodiment of the present invention.

Figure 3A:
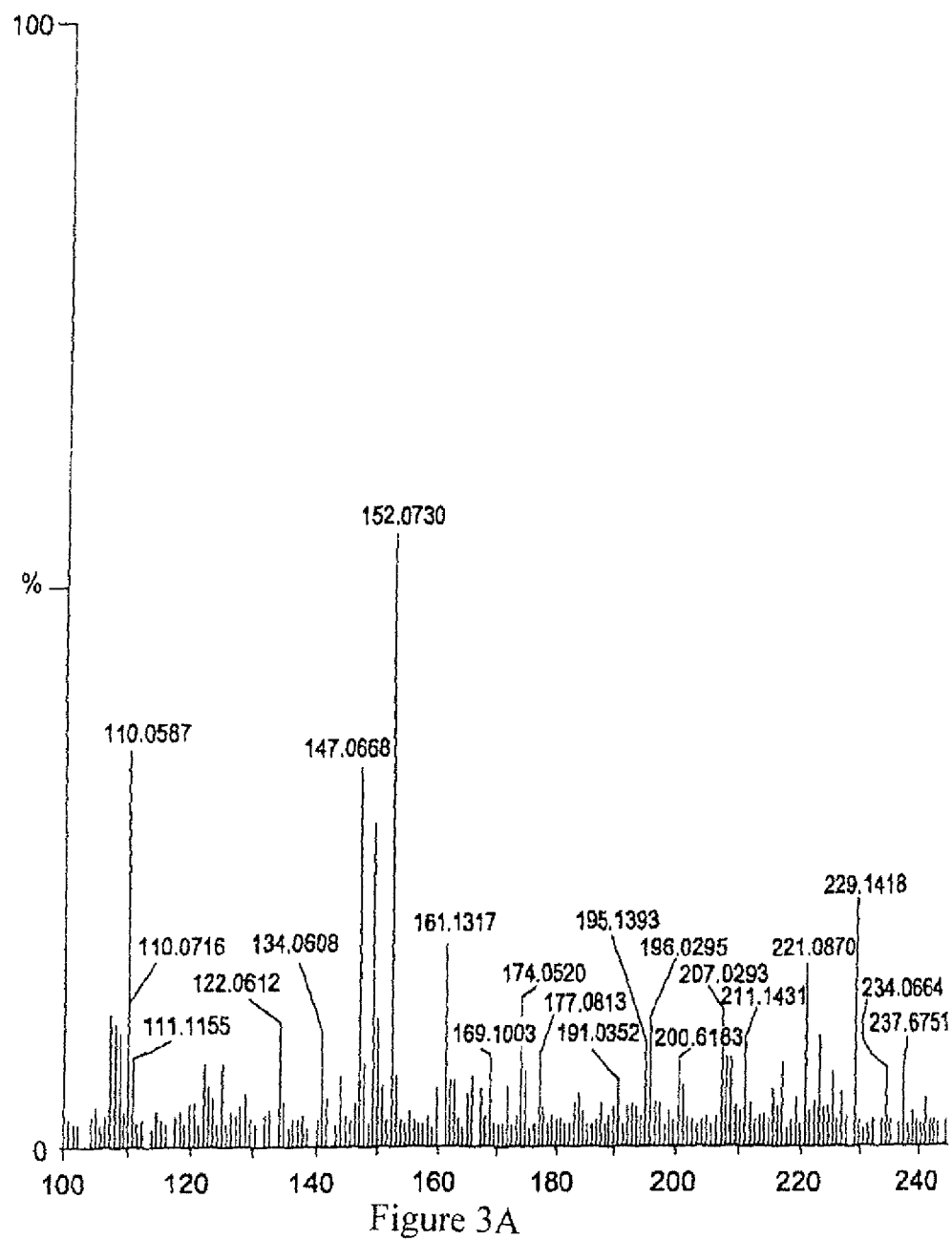
FIGS. 3A, 3B and 3C show a mass spectrum obtained according to preferred embodiment of the present invention wherein a paracetamol tablet is analysed to detect its ingredients.
Figure 3B:
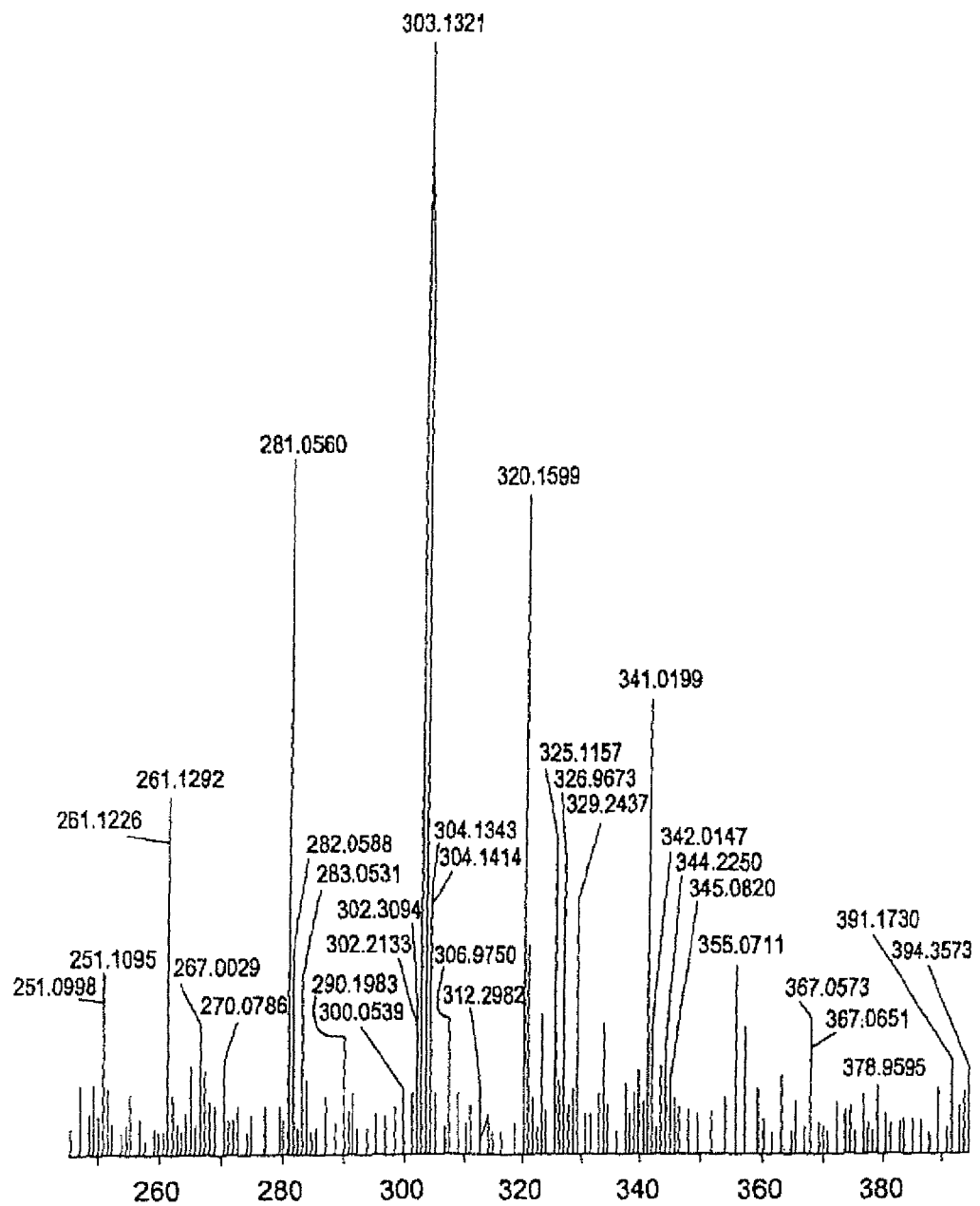
Figure 3C:
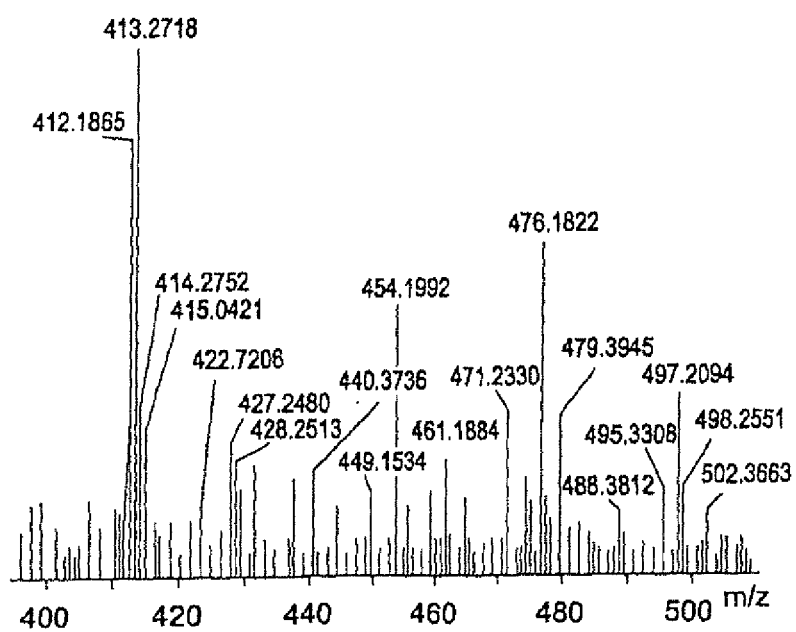

FIG. 3 shows FIGS. 3A, 3B and 3C show a mass spectrum which was obtained when analysing one half of a paracetamol tablet which had been moistened on its surface with a few drops of a 50% mixture of methanol and water (0.1% formic acid) using an electric knife according to an embodiment of the present invention.

FIG. 3 shows FIGS. 3A, 3B and 3C show that the active compound of the paracetamol tablet was clearly detected at m/z 152.0709 (−2 ppm) and ions from the bulk of the tablet are also clearly visible in the mass spectrum.

It is apparent that the preferred method of detecting one or more compounds, chemicals or contaminants in a substrate by a method of mass spectrometry is particularly advantageous and may advantageously be implemented using a portable mass analyser.

Other less preferred embodiments of the present invention are also contemplated wherein the electrosurgical knife may be replaced with a different device which is preferably used to vaporise at least a portion of the sample. For example, according to an embodiment an ultrasonic probe may be utilised to probe a substrate and generate a plume of gas phase analyte molecules which are preferably transferred into a vacuum chamber of a mass spectrometer and ionised by impact ionisation with a surface within the vacuum chamber.

According to another embodiment a laser probe may be used to generate gas phase analyte molecules which are preferably transferred into a vacuum chamber of a mass spectrometer and ionised by impact ionisation with a surface within the vacuum chamber.

According to another embodiment a jet of fluid may be directed onto a substrate to generate gas phase analyte molecules which are preferably transferred into a vacuum chamber of a mass spectrometer and ionised by impact ionisation with a surface within the vacuum chamber.

It is should be understood that the various preferred features of the preferred embodiment relating to the electrosurgical knife also apply to the less preferred embodiments relating to using an ultrasonic probe, a laser probe of a jet of fluid. In particular, gas phase analyte molecules resulting from the substrate being probed with an ultrasonic probe, a laser probe or a jet of fluid may be aspirated via a tube into an initial or subsequent vacuum chamber of a mass spectrometer whereupon the analyte molecules are ionised by impacting a surface e.g. a wall of the vacuum chamber and/or an RF ion-optical component such as an ion guide or ion trap. The less preferred devices may be used to perform all the testing procedures which are described above in relation to using an RF surgical knife. The apparatus and method according to the present invention is not used to perform a surgical or therapeutic procedure.

Although the present invention has been described with reference to the preferred embodiments, it will be understood by those skilled in the art that various changes in form and detail may be made without departing from the scope of the invention as set forth in the accompanying claims.

The invention claimed is:

1. A non-surgical method of mass spectrometry comprising:
    probing a substrate with an electrode, a jet of fluid, or a laser probe at atmospheric pressure to cause a portion of the substrate to vaporise to generate a plurality of gas-phase analyte molecules, wherein the substrate comprises a food product;
    transporting at least a portion of the generated gas-phase analyte molecules into a vacuum chamber of a mass spectrometer, wherein a surface of the vacuum chamber is arranged for ionising analyte molecules;
    causing at least a portion of the generated gas-phase analyte molecules to be ionized by impacting upon said surface of the vacuum chamber of the mass spectrometer to form analyte ions;
    mass analysing at least a portion of the analyte ions; and further comprising detecting if one or more contaminants are present in the substrate above a predetermined concentration.

2. A method as claimed in claim 1, wherein the electrode comprises an electrode of a diathermy knife or an electrosurgical RF knife.

3. A method as claimed in claim 1, further comprising aspirating the analyte molecules via a tube or supply line into the mass spectrometer.

4. A method as claimed in claim 1, further comprising using a pump to draw the analyte molecules into the mass spectrometer, wherein the pump is not directly connected to an exhaust port of a vacuum chamber.

5. A method as claimed in claim 1, wherein at least a portion of the analyte molecules are ionised upon impacting an RF ion-optical component located within the vacuum chamber.

6. A method as claimed in claim 1, wherein a portion of the analyte molecules are ionised by an ion source located within the vacuum chamber.

7. A method as claimed in claim 1, wherein the step of probing the substrate with the probe generates a mixture of analyte molecules and droplets, the method comprising:
transporting at least a portion of the mixture into the vacuum chamber of the mass spectrometer; and
mass analysing at least a portion of the analyte ions and the droplets or at least a portion of further analyte ions derived from the droplets.

8. A method as claimed in claim 1, comprising using a portable mass spectrometer to perform the step of mass analysing at least a portion of the analyte ions.

9. A method as claimed in claim 1, wherein the substrate comprises a solid, gel or powder.

10. A method as claimed in claim 1, wherein said contaminant is selected from the group comprising: (i) a pesticide; (ii) a steroid; (iii) chloramphenicol; (iv) a bulking material; or (v) a mycotoxin.

11. A method as claimed in claim 1, wherein said contaminant comprises histamine, putrescine or cadaverine.

12. A method as claimed in claim 1, further comprising determining a freshness of the food product.

13. A method of mass spectrometry comprising:
probing a substrate with an electrode, a jet of fluid, or a laser probe at atmospheric pressure to cause a portion of the substrate to vaporise to generate a plurality of gas-phase analyte molecules;
transporting at least a portion of the generated gas-phase analyte molecules into a vacuum chamber of a mass spectrometer, wherein a surface of the vacuum chamber is arranged for ionising analyte molecules;
causing at least a portion of the generated gas-phase analyte molecules to be ionized by impacting upon said surface of the vacuum chamber of the mass spectrometer to form analyte ions; and
mass analysing at least a portion of the analyte ions.

14. A method as claimed in claim 13, wherein the substrate comprises a food product, the method further comprising determining a freshness of the food product.

15. A non-surgical method of mass spectrometry comprising:
probing a substrate with an electrode, a jet of fluid, or a laser probe at atmospheric pressure to cause a portion of the substrate to vaporise to generate a plurality of gas-phase analyte molecules;
transporting at least a portion of the generated gas-phase analyte molecules into a vacuum chamber of a mass spectrometer, wherein a surface of the vacuum chamber is arranged for ionising analyte molecules;
causing at least a portion of the generated gas-phase analyte molecules to be ionized by impacting upon said surface of the vacuum chamber of the mass spectrometer to form analyte ions; and
mass analysing at least a portion of the analyte ions;
wherein the substrate comprises a pharmaceutical tablet and wherein the method comprises detecting one or more active ingredients or bulking agents in the substrate.

* * * * *